(12) United States Patent
Campbell et al.

(10) Patent No.: US 10,309,901 B2
(45) Date of Patent: Jun. 4, 2019

(54) WATER-SENSITIVE FLUOROPHORES FOR MOISTURE CONTENT EVALUATION IN HYGROSCOPIC POLYMERS

(71) Applicant: International Business Machines Corporation, Armonk, NY (US)

(72) Inventors: Eric J. Campbell, Rochester, MN (US); Sarah K. Czaplewski, Rochester, MN (US); Joseph Kuczynski, North Port, FL (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 15/436,376

(22) Filed: Feb. 17, 2017

(65) Prior Publication Data

US 2018/0238801 A1    Aug. 23, 2018

(51) Int. Cl.
| | |
|---|---|
| G01N 21/64 | (2006.01) |
| G01N 21/81 | (2006.01) |
| G01N 33/44 | (2006.01) |
| G01N 33/18 | (2006.01) |
| G01N 21/77 | (2006.01) |

(52) U.S. Cl.
CPC .......... *G01N 21/643* (2013.01); *G01N 21/81* (2013.01); *G01N 33/18* (2013.01); *G01N 33/442* (2013.01); *G01N 2021/6443* (2013.01); *G01N 2021/7786* (2013.01)

(58) Field of Classification Search
CPC ...... G01N 21/643; G01N 21/81; G01N 33/18; G01N 33/442

USPC ............................................ 436/39, 42, 172
See application file for complete search history.

(56) References Cited

U.S. PATENT DOCUMENTS

| | | | | |
|---|---|---|---|---|
| 4,681,576 A | * | 7/1987 | Colon | ...................... A61F 13/42 604/361 |
| 4,743,238 A | * | 5/1988 | Colon | ...................... A61F 13/42 604/361 |
| 4,895,567 A | * | 1/1990 | Colon | ...................... A61F 13/15 604/361 |
| 4,990,284 A | | 2/1991 | Lauterbach et al. | |

(Continued)

FOREIGN PATENT DOCUMENTS

DE         19942317 A1    4/2001

OTHER PUBLICATIONS

Shea, K. J. et al, Macromolecules 1989, 22, 1722-1730.*

(Continued)

*Primary Examiner* — Arlen Soderquist
(74) *Attorney, Agent, or Firm* — Rochester Patent Center

(57) ABSTRACT

A process of utilizing a water-sensitive fluorophore for moisture content evaluation in a hygroscopic polymer includes forming a blend that includes a hygroscopic polymer resin and a water-sensitive fluorophore. The process includes forming pellets having a particular geometry from the blend, determining fluorescence properties of at least one of the pellets, and determining moisture content of at least one of the pellets. The process also includes generating a calibration curve for the particular pellet geometry by correlating the fluorescence properties with the moisture content. The process further includes providing the calibration curve for non-destructive moisture content evaluation of a material derived from the pellets.

20 Claims, 4 Drawing Sheets

(56) References Cited

U.S. PATENT DOCUMENTS

| | | | |
|---|---|---|---|
| 5,244,813 A * | 9/1993 | Walt | G01N 21/7703 385/12 |
| 5,336,714 A | 8/1994 | Krutak et al. | |
| 5,342,861 A * | 8/1994 | Raykovitz | A61L 15/56 523/111 |
| 5,458,896 A | 10/1995 | Porter | |
| 6,499,355 B1 * | 12/2002 | Potyrailo | G01B 11/20 73/150 A |
| 6,953,345 B1 * | 10/2005 | Nakashima | B43K 8/02 434/408 |
| 7,002,079 B2 | 2/2006 | Mitchell et al. | |
| 2004/0196734 A1 * | 10/2004 | Mehta | B01F 3/10 366/138 |
| 2005/0133697 A1 * | 6/2005 | Potyrailo | C08L 69/00 250/216 |
| 2006/0199270 A1 * | 9/2006 | Parnas | G01N 21/643 436/127 |
| 2007/0264420 A1 * | 11/2007 | Davies | B42C 9/00 427/8 |
| 2009/0023200 A1 | 1/2009 | Nishino et al. | |
| 2010/0022759 A1 * | 1/2010 | Yamauchi | A61K 49/0021 530/402 |
| 2010/0264369 A1 * | 10/2010 | Zhang | A61L 15/56 252/301.35 |
| 2013/0210156 A1 * | 8/2013 | Wooley | A61B 5/14539 436/63 |
| 2017/0183705 A1 * | 6/2017 | Hicks | C08G 18/10 |

OTHER PUBLICATIONS

Barnard, S. M. et al, Environmental Science and Technology 1991, 25, 1301-1304.*
Sadaoka, Y. et al, Chemistry Letters 1992, 53-56.*
Potyrailo, R. A. et al, Fresenius Journal of Analytical Chemistry 1999, 364, 32-40.*
Otsuki et al., "Medium-Sensitive Fluorophore as a Moisture Probe in Polymer Film", published in the Polymer Journal, vol. 26, Issue 3, Mar. 1994, pp. 343-48, Nature Research (online, nature.com), URL: www.nature.com/pj/journal/v26/n3/pdf/pj199441a.pdf.
Sepe, "The Materials Analyst, Part 85: Fixing brittle nylon product with water", PlasticsToday.com (online), Apr. 30, 2007, 4 pages, URL: www.plasticstoday.com/materials-analyst-part-85-fixing-brittle-nylon-product-water/1246717263500/page/0/1.
Wikipedia, "Reichardt's Dye", Wikipedia.org (online), [accessed Oct. 11, 2016], 2 pages, URL: en.wikipedia.org/wiki/Reichardt's_dye?previous=yes.
Vertucci et al., "Chlorophyll Fluorescence Characteristics Associated with Hydration Level in Pea Cotyledons", Plant Physiology, vol. 79, Issue 1, Sep. 1985, pp. 248-252, American Society of Plant Biologists (online, aspb.org), URL: www.plantphysiol.org/content/79/1/248.full.pdf+html?sid=8c66c750-63fd-4e9f-b9b6-ae8524123a84.

* cited by examiner

US 10,309,901 B2

WATER-SENSITIVE FLUOROPHORES FOR MOISTURE CONTENT EVALUATION IN HYGROSCOPIC POLYMERS

BACKGROUND

Hygroscopic polymers, such as nylon polymers, have a high affinity for water due to polar bonds in such polymers (e.g., polar amide bonds in the case of nylon polymers). Typically, such polymers may hold approximately 1.5 to 2 percent of their weight in water. However, this weight percentage may be substantially higher if the polymer is stored at high humidity or is immersed in water. Controlling the water content in hygroscopic polymers, such as nylon polymers, is important not only during manufacturing (e.g., via injection molding) but also in the final article of manufacture. Other examples of hygroscopic polymers include acrylonitrile butadiene styrene (ABS) polymers, acrylics, polyurethanes, polyethylene terephthalate (PET), and polybutylene terephthalate (PBT), among others.

Prior to injection molding, resin pellets are dried in order to mitigate problems associated with the presence of water, such as chain degradation, decreased molecular weight, and ultimately degraded mechanical properties in the final article of manufacture. Therefore, understanding the moisture content of the resin pellets is important. While drying the resin pellets is important prior to injection molding, the presence of at least some moisture in the final article of manufacture may be desirable in some cases (e.g., for toughness and/or flexibility). In hygroscopic polymers, water acts as a plasticizer, spacing out the polymer chains, reducing the glass transition temperature, and making the article of manufacture more flexible. Accordingly, after manufacture, a nylon article may be moisture conditioned or allowed to reach its equilibrium moisture content before being used in applications where high loads are generated. Otherwise, brittle fracture of the nylon article may result. Furthermore, depending on the environment, a nylon article may dry out over time, potentially resulting in future failure of the nylon article after field deployment. As such, monitoring of moisture content in the final article after field deployment may also be required in order to prevent the possibility of failure as a result of the article drying out (e.g., in a high temperature and/or low humidity environment).

SUMMARY

According to an embodiment, a process of utilizing a water-sensitive fluorophore for moisture content evaluation in a hygroscopic polymer is disclosed. The process includes forming a blend that includes a hygroscopic polymer resin and a water-sensitive fluorophore. The process includes forming pellets having a particular geometry from the blend, determining fluorescence properties of at least one of the pellets, and determining moisture content of at least one of the pellets. The process also includes generating a calibration curve for the particular pellet geometry by correlating the fluorescence properties with the moisture content. The process further includes providing the calibration curve for non-destructive moisture content evaluation of a material derived from the pellets.

According to another embodiment, a process of utilizing a water-sensitive fluorophore for moisture content evaluation in a hygroscopic polymer is disclosed. The process includes receiving pellets from a pellet manufacturing entity. The pellets are formed from a blend that includes a hygroscopic polymer resin and a water-sensitive fluorophore. The process also includes receiving a calibration curve from the pellet manufacturing entity that correlates fluorescence properties of the pellets with moisture content of the pellets. The process further includes measuring fluorescence properties of the dried pellets and utilizing the calibration curve to determine a moisture content level of the dried pellets based on the measured fluorescence properties of the dried pellets. The process also includes determining whether to form the article of manufacture from the dried pellets based on whether the moisture content level of the dried pellets corresponds to a satisfactory moisture level.

According to another embodiment, a process of utilizing a water-sensitive fluorophore for moisture content evaluation in a hygroscopic polymer is disclosed. The process includes measuring fluorescence properties of an article of manufacture that is deployed to a deployment environment. The article of manufacture is manufactured from pellets that are formed from a blend that includes a hygroscopic polymer resin and a water-sensitive fluorophore. The process also includes receiving a part-specific calibration curve that correlates fluorescence properties of the article of manufacture with moisture content of the article of manufacture. The process further includes utilizing the part-specific calibration curve to determine a moisture content level of the article of manufacture based on the measured fluorescence properties of the article of manufacture. The process also includes determining whether to perform a corrective action based on whether the moisture content level of the article of manufacture corresponds to a satisfactory moisture level.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes water-sensitive fluorophores for moisture content evaluation in hygroscopic polymers. A water sensitive fluorophore may be mixed with a hygroscopic polymer resin to form a blend, and the blend may be used to form pellets. The pellets may be analyzed to determine fluorescence properties and moisture content for the particular pellet geometry, which may be used to generate a calibration curve for subsequent non-destructive moisture content evaluation. In some cases, a part manufacturing entity may utilize the calibration curve to non-destructively determine moisture content. For example, the part manufacturing entity may verify that the pellets (that include the water sensitive fluorophore and the hygroscopic polymer) have been sufficiently dried prior to forming an article of manufacture from the pellets (e.g., via injection molding). In some cases, the part manufacturing entity may analyze the article of manufacture to determine fluorescence properties for the particular part geometry, which may be used to generate a part-specific calibration curve. In some cases, a part monitoring entity may utilize the part-specific calibration curve to non-destructively determine moisture content of the article of manufacture after deployment of the article to a deployment environment having a particular set of environmental conditions (e.g., high temperature and/or low humidity). In the event that the moisture content of the deployed article is unsatisfactory and may potentially lead to fracture/failure of the field-deployed article, the part monitoring entity may perform a corrective action (e.g., removing/replacing the deployed article). Thus, the present disclosure describes various examples of the utilization of water-sensitive fluorophores with hygroscopic polymers for non-destructive moisture content evaluation.

Figure 1:
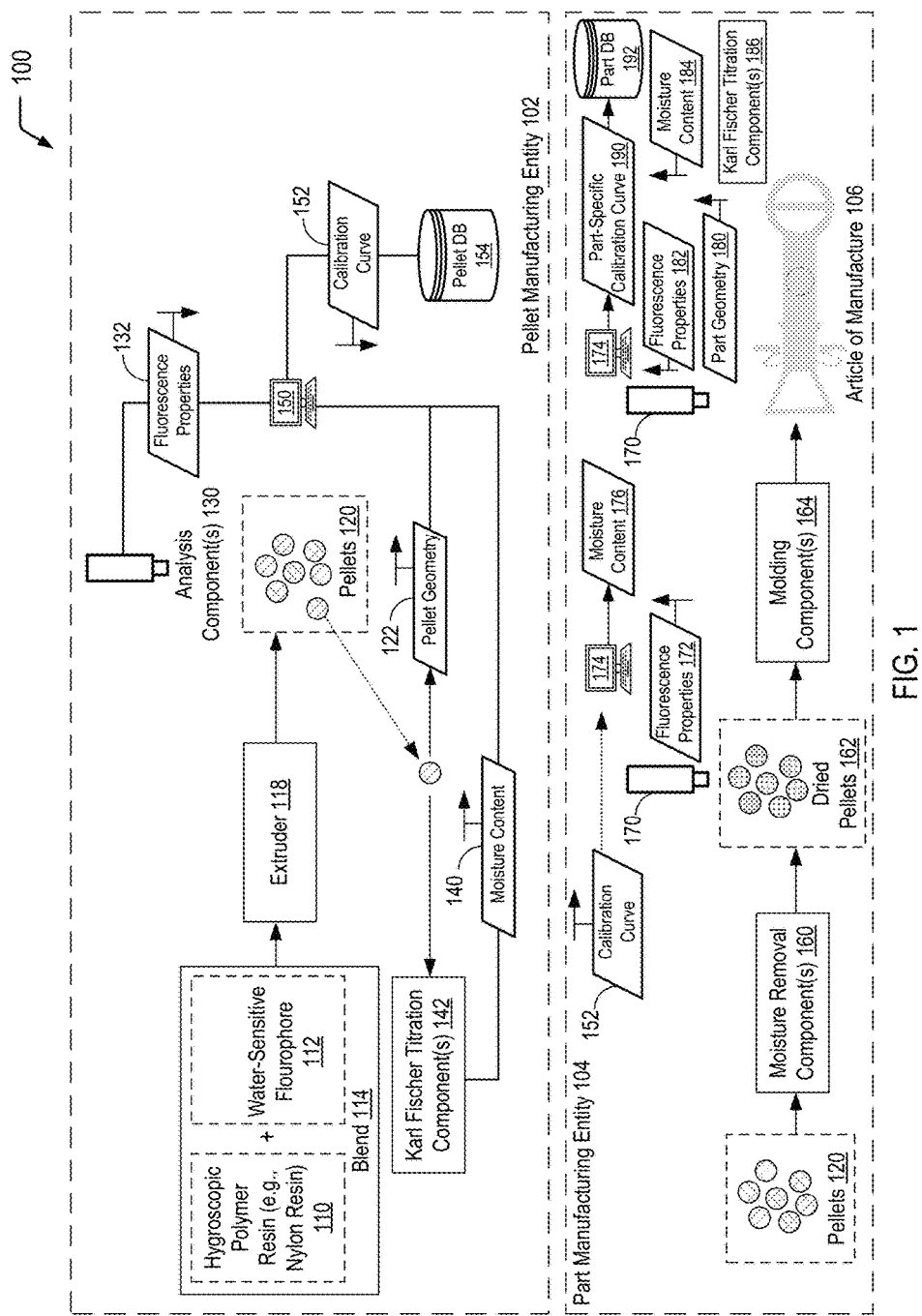
FIG. 1 is a diagram illustrating a system of utilizing water-sensitive fluorophores with hygroscopic polymers for determining whether a moisture content level is satisfactory, according to one embodiment.

Referring to FIG. 1, a diagram 100 illustrates an example of a system of utilizing water-sensitive fluorophores with hygroscopic polymers for determining whether a moisture content level is satisfactory, according to one embodiment. In the particular embodiment depicted in FIG. 1, dashed lines are used to indicate that a first set of operations may be performed by a first entity (e.g., a pellet manufacturing entity 102), and a second set of operations may be performed by a second entity (e.g., a part manufacturing entity 104). In the example of FIG. 1, the pellet manufacturing entity 102 performs operations to generate data that may be utilized by the part manufacturing entity 104 to determine whether sufficient moisture removal has occurred prior to the formation of an article of manufacture 106 (e.g., prior to an injection molding operation). FIG. 1 further illustrates that, after forming the article of manufacture 106, the part manufacturing entity 104 may perform operations to generate data that may be used to generate a part-specific calibration curve 190 corresponding to the particular geometry of the article of manufacture 106. As illustrated and further described herein with respect to FIG. 2, another entity (e.g., a part monitoring entity) may utilize the part-specific calibration curve 190 generated by the part manufacturing entity 104 to non-destructively monitor the moisture content after deployment of the article of manufacture 106.

In the particular embodiment depicted in FIG. 1, a hygroscopic polymer resin 110 is mixed with a water-sensitive fluorophore 112 to form a blend 114. In a particular embodiment, the hygroscopic polymer resin 110 may include a nylon resin (e.g., a nylon 6,6 resin). Alternatively or additionally, the hygroscopic polymer resin 110 may include an ABS polymer resin, an acrylic resin, a polyurethane resin, a PET resin, or a PBT resin, among other examples. With respect to the water-sensitive fluorophore 112, illustrative examples may include 5-(dimethylamino)naphthalene-1-sulfonic acid (DNSA), 5-(dimethylamino)naphthalene-1-sulfonamide (DNSM), 8-(anilino)naphthalene-1-sulfonic acid (ANSA), or a combination thereof, among other alternatives.

In the example of FIG. 1, the water-sensitive fluorophore 112 is compounded into the hygroscopic polymer resin 110 using an extruder 118 to form pellets 120. It will be appreciated that alternative pellet formation component(s) and/or pellet formation techniques may be utilized in other cases. The pellets 120 formed from the blend 114 have a particular pellet geometry 122. FIG. 1 illustrates that one or more analysis components 130 may be utilized to determine one or more fluorescence properties 132 of the pellets 120 having the particular geometry 122. The fluorescence properties 132 of the pellets 120 may include fluorescence intensity data and/or emission maximum data for a particular concentration of the water-sensitive fluorophore 112 in the blend 114, among other examples of fluorescence data.

FIG. 1 illustrates that a moisture content 140 of the pellets 120 may be determined via Karl Fischer titration. For ease of illustration purposes, the determination of the moisture content 140 via Karl Fischer titration is depicted as being performed by one or more Karl Fischer titration components 142. Further, while FIG. 1 illustrates such testing being performed on one of the pellets 120, it will be appreciated that such testing may be performed on more than one of the pellets 120.

In the example of FIG. 1, the fluorescence properties 132 determined by the analysis component(s) 130 and the moisture content 140 determined by the Karl Fischer titration component(s) 142 may be provided to a computing device 150. The computing device 150 may generate a calibration curve 152 for the particular pellet geometry 122 by correlating the fluorescence properties 132 with the moisture content 140. The calibration curve 152 may be stored in a pellet database 154 for subsequent use by the part manufacturing entity 104 for non-destructive verification of sufficient drying of the pellets 120 prior to molding the article of manufacture 106, as described further herein with respect to FIG. 1.

The bottom of FIG. 1 (delineated by the dashed lines) illustrates subsequent operations performed by the part manufacturing entity 104 using the pellets 120 formed by the pellet manufacturing entity 102. Prior to forming the article of manufacture 106 (e.g., by injection molding), the part manufacturing entity 104 may utilize one or more moisture removal components 160 to remove moisture from the pellets 120 to form dried pellets 162. After determining that the dried pellets 162 have a satisfactory moisture content, the part manufacturing entity 104 may utilize one or more molding components 164 to form the article of manufacture 106. The bottom of FIG. 1 further illustrates that the part manufacturing entity 104 may analyze the article of manufacture 106 to generate a part-specific calibration curve 190 for the article of manufacture 106 for subsequent non-destructive monitoring of the moisture content after the article of manufacture 106 has been field-deployed.

The part manufacturing entity 104 may utilize one or more analysis components 170 (that may be the same or similar to the analysis component(s) 130 utilized by the pellet manufacturing entity 102) to determine fluorescence properties 172 of the dried pellets 162. A computing device 174 may utilize the calibration curve 152 generated by the pellet manufacturing entity 102 to determine a moisture content 176 of the dried pellets 162 based on the fluorescence properties 172 of the dried pellets 162. The part manufacturing entity 104 may determine whether the moisture content 176 for the dried pellets 162 is satisfactory prior to utilizing the one or more molding components 164 to form the article of manufacture 106. In this case, a satisfactory moisture content may correspond to a sufficiently low level of moisture in the dried pellets 162 in order to prevent hydrolysis and subsequent embrittlement of the article of manufacture 106 following injection molding.

When the moisture content 176 of the dried pellets 172 is satisfactory for molding operations (e.g., injection molding operations), the part manufacturing entity 104 may utilize the molding component(s) 164 to form the article of manufacture 106. When the moisture content 176 of the dried pellets 162 is unsatisfactory, the part manufacturing entity 104 may perform additional drying operation(s) using the moisture removal component(s) 160. The analysis component(s) 170 may be utilized to determine subsequent fluorescence properties after the additional drying operation(s), and the operations may be repeated until the measured fluorescence properties are indicative of a satisfactory moisture content.

FIG. 1 further illustrates that, after forming the article of manufacture 106, the part manufacturing entity 104 may analyze the article of manufacture 106 to generate the part-specific calibration curve 190 that corresponds to a particular part geometry 180 of the article of manufacture 106. While not shown in the example of FIG. 1, after forming the article of manufacture 106 using the molding component(s) 164, the article of manufacture 106 may be moisture conditioned or allowed to reach its equilibrium moisture content before analyzing the article of manufacture 106 to generate the part-specific calibration curve 190. Thus, while FIG. 1 illustrates sequential operations being performed by the part manufacturing entity 104, it will be appreciated that additional operation(s) may be performed after the molding the article of manufacture 106 and that there may be a time delay between the formation of the article of manufacture 106 and the subsequent analysis of the article of manufacture 106.

FIG. 1 illustrates that the analysis component(s) 170 may be utilized to determine one or more fluorescence properties 182 of the article of manufacture 106 having the particular part geometry 180. To illustrate, the fluorescence properties 182 of the article of manufacture 106 may include fluorescence intensity data and/or emission maximum data, among other examples of fluorescence data. In the particular embodiment depicted in FIG. 1, a dashed line is used to indicate that a particular area of the article of manufacture 106 may be selected for measurement of the fluorescence properties 182. In some cases, as illustrated and further described herein with respect to FIG. 2, the particular area may be identified as a target area for measurement of fluorescence properties after the article of manufacture 106 has been field-deployed.

FIG. 1 further illustrates that a moisture content 184 of the article of manufacture 106 may be determined via Karl Fischer titration using one or more Karl Fischer titration component(s) 186. While FIG. 1 illustrates such testing being performed on a single article having the particular part geometry 180, it will be appreciated that such testing may be performed on multiple articles.

FIG. 1 illustrates an example in which the fluorescence properties 182 determined by the analysis component(s) 170 and the moisture content 184 determined by the Karl Fischer titration component(s) 186 may be provided to the computing device 174 (which may be the same computing device that is utilized during the analysis of the dried pellets 162 or a different computing device). The computing device 174 may generate the part-specific calibration curve 190 for the particular part geometry 180 by correlating the fluorescence properties 182 with the moisture content 184. The part-specific calibration curve 190 may be stored in a part database 192 for subsequent non-destructive moisture content verification (e.g., after the article of manufacture 106 has been field-deployed, as illustrated and described further herein with respect to FIG. 2).

Thus, FIG. 1 illustrates an example of a system of utilizing water-sensitive fluorophores with hygroscopic polymers for determining whether a moisture content level is satisfactory. A pellet manufacturing entity may utilize measured fluorescence properties and moisture content to generate a calibration curve for a particular pellet geometry. Subsequently, a part manufacturing entity may measure fluorescence properties and utilize the calibration curve to non-destructively determine moisture content based on the measured fluorescence properties. In the example of FIG. 1, the part manufacturing entity may perform additional pellet drying operations when a pellet moisture content level is considered unsatisfactory for injection molding to form an article of manufacture. FIG. 1 further illustrates that, after the article of manufacture has been formed, the part manufacturing entity may measure fluorescence properties and moisture content of the article to generate a part-specific calibration curve for a particular part geometry. As illustrated and further described herein with respect to FIG. 2, a part monitoring entity may utilize the part-specific calibration curve to non-destructively determine moisture content based on measured fluorescence properties of a field-deployed article.

Figure 2:
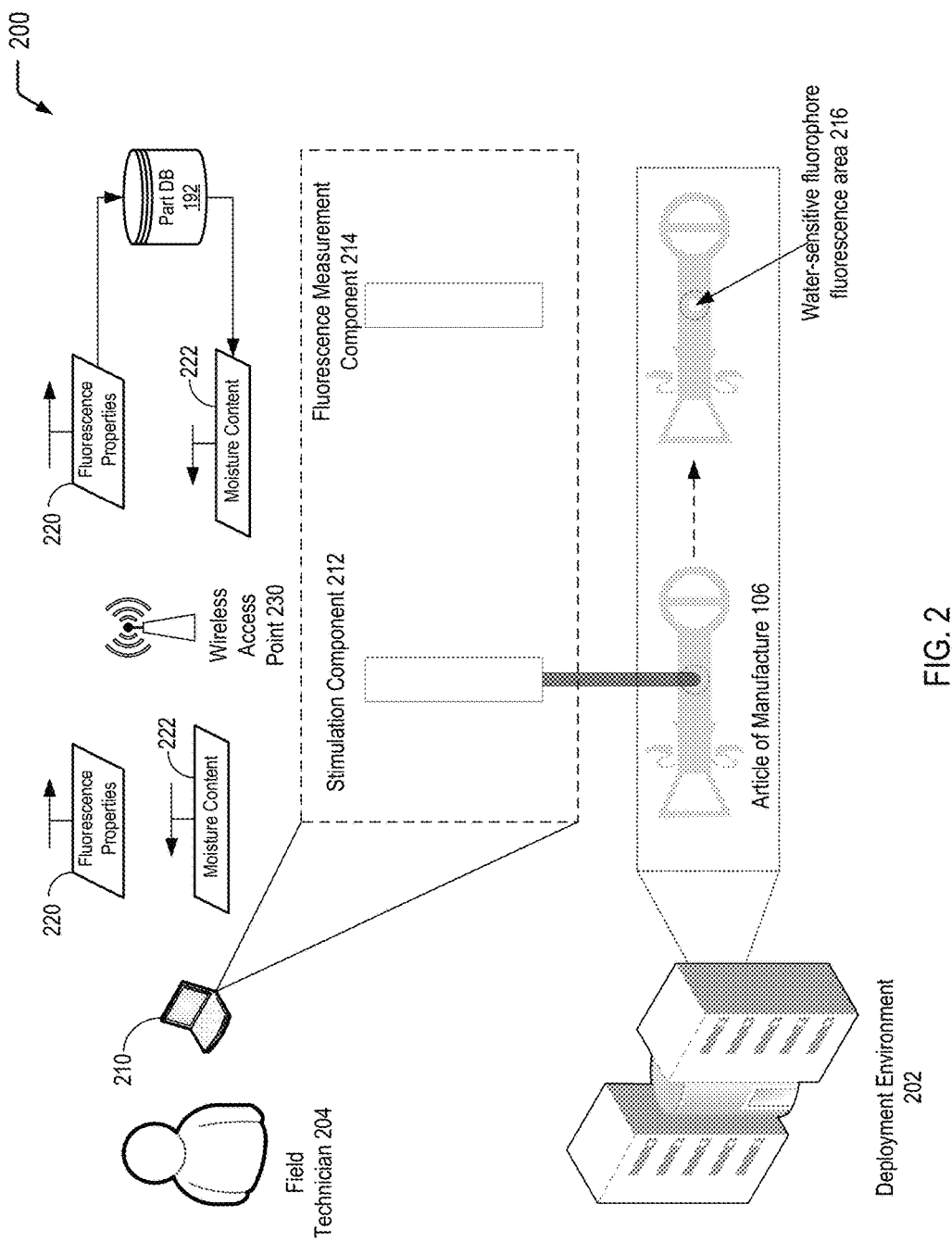
FIG. 2 is a diagram illustrating a system of determining whether a moisture content level of an article of manufacture that includes water-sensitive fluorophores is satisfactory, according to one embodiment.

Referring to FIG. 2, a diagram 200 illustrates an example of a system of determining whether a moisture content level of an article of manufacture that includes water-sensitive fluorophores is satisfactory, according to one embodiment. In a particular embodiment, the article of manufacture may correspond to the article of manufacture 106 formed by the part manufacturing entity 104, as previously described herein with respect to FIG. 1. FIG. 2 illustrates that the addition of the water-sensitive fluorophore 112 to the hygroscopic polymer resin 110 may enable non-destructive testing of moisture content after field deployment of the article of manufacture 106.

In FIG. 2, the article of manufacture 106 has been deployed to a deployment environment 202. As an illustrative, non-limiting example, the article of manufacture 106 may include a nylon pull tab (e.g., a nylon 6,6 pull tab) for cable management behind a server rack. In this example, the article of manufacture 106 may experience high temperature and/or low humidity conditions as a result of the server exhaust. In some cases, such environmental conditions may cause the article of manufacture 106 to embrittle as a result of moisture removal, potentially resulting in fracture/failure of the article of manufacture 106. Accordingly, monitoring the moisture content in the deployment environment 202 in a non-destructive manner may enable an entity (e.g., a field technician 204 associated with a part monitoring entity) to determine whether the moisture content in the deployment environment 202 is a cause for a potential corrective action (e.g., removal and/or replacement of the article of manufacture 106).

FIG. 2 illustrates an example in which the field technician 204 may utilize a computing device 210 that includes or is otherwise communicatively coupled to a stimulation component 212 and a fluorescence measurement component 214 for non-destructive moisture content evaluation in the article of manufacture 106 in the deployment environment 202. The stimulation component 212 (e.g., a laser light tuned according to the particular fluorescence profile of the water-sensitive fluorophore 112) may be utilized to stimulate the water-sensitive fluorophore 112 in the article of manufacture 106. FIG. 2 illustrates that stimulation of a particular area of the article of manufacture 106 by the stimulation component 212 results in a water-sensitive fluorophore fluorescence area 216. The fluorescence measurement component 214 may measure fluorescence properties 220 associated with the water-sensitive fluorophore fluorescence area 216. As previously described herein, the dashed lines illustrated in the example of FIG. 2 may represent a target area for testing to assist the field technician 204 in obtaining accurate fluorescence data for moisture content determination.

The measured fluorescence properties 220 may be utilized to determine, in a non-destructive manner, a moisture content 222 of the article of manufacture 106 in the deployment environment 202. In the particular embodiment depicted in FIG. 2, the field technician 204 may utilize the computing device 210 to communicate, via a wireless access point 230 (or other network connection equipment), the fluorescence properties 220 to the part database 192. As previously described herein, the part-specific calibration curve 190 generated by the part manufacturing entity 104 may be stored in the part database 192. FIG. 2 illustrates that the part-specific calibration curve 190 (stored at the part database 192) may be utilized to determine the moisture content 222 that is associated with the particular fluorescence properties 220 as measured for the article of manufacture 106 in the deployment environment 202.

In some cases, the field technician 204 may evaluate the moisture content 222 to determine whether the moisture content 222 represents a satisfactory moisture level for the article of manufacture 106 in the deployment environment 202. In other cases, the moisture content 222 may be automatically compared to a satisfactory moisture content level stored at the computing device 210 in order to alert the field technician 204 that a corrective action may be appropriate. As an example of a corrective action, the field technician 204 may remove the article of manufacture 106 from service and/or replace the article of manufacture 106 with another article that is known to have a satisfactory moisture level.

In some cases, when the moisture content 222 is considered to be satisfactory for the article of manufacture 106 in the deployment environment 202, the field technician 204 may take no action or may schedule a subsequent time for moisture content monitoring (e.g., in cases where periodic monitoring may be advantageous), among other possibilities. In other cases, the field technician 204 may identify the article of manufacture 106 as being able to maintain a satisfactory moisture level in the particular environmental conditions associated with the deployment environment 202.

Thus, FIG. 2 illustrates an example of a system of determining whether a moisture content level of an article of manufacture that includes a water-sensitive fluorophore is satisfactory. The ability to monitor the moisture content of a part that is deployed to a particular deployment environment in a non-destructive manner may enable a determination of whether the moisture content is satisfactory or is a cause for corrective action.

Figure 3:
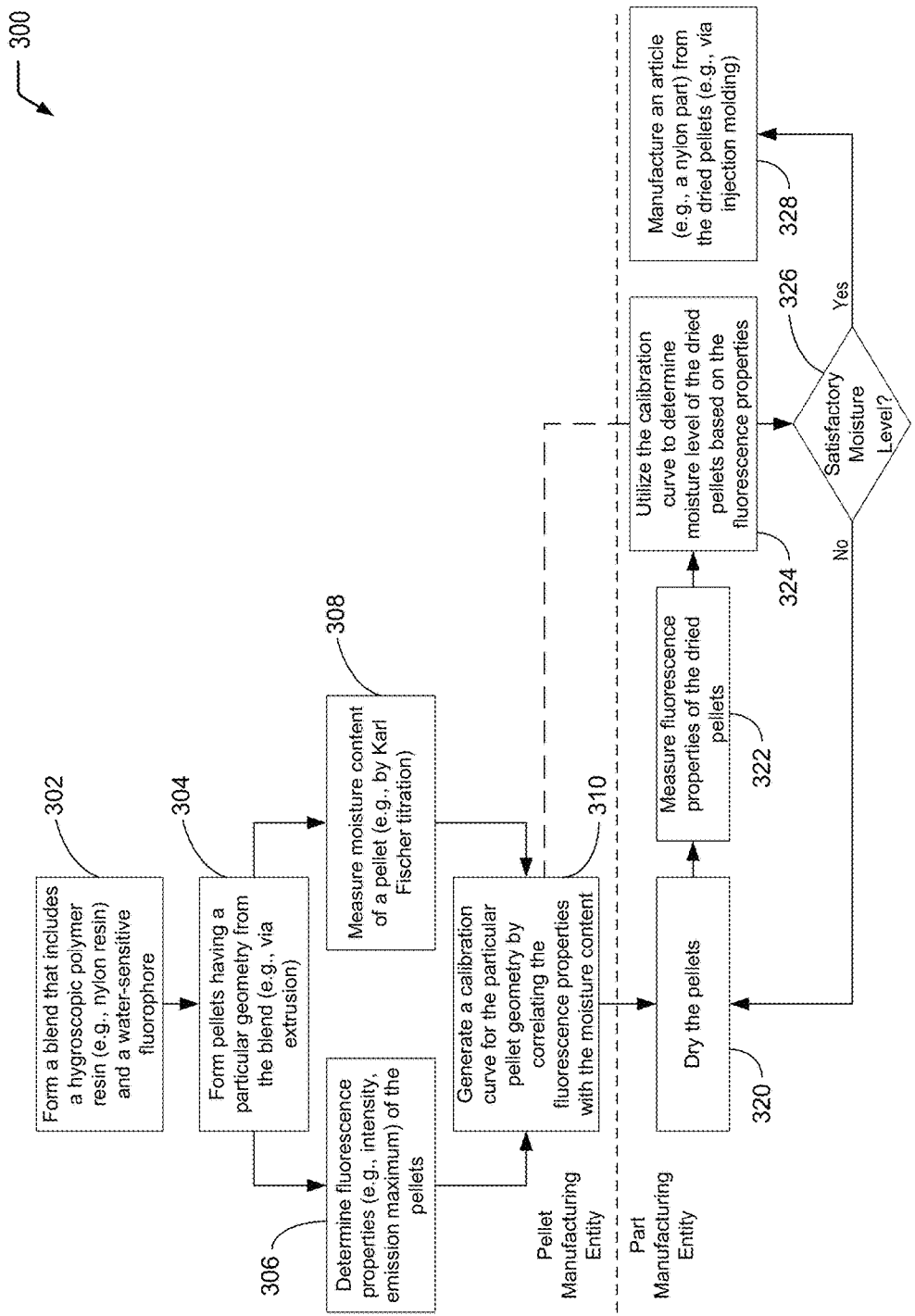
FIG. 3 is a flow diagram depicting a particular embodiment of a process of utilizing water-sensitive fluorophores with hygroscopic polymers for determining whether moisture content level is satisfactory.

Referring to FIG. 3, a flow diagram illustrates an example of a process 300 of utilizing water-sensitive fluorophores with hygroscopic polymers for determining whether moisture content level is satisfactory, according to one embodiment. FIG. 3 illustrates (via a dashed line) that, in some cases, a first set of operations (e.g., operations 302-310) may be performed by one entity (e.g., a pellet manufacturing entity, such as the pellet manufacturing entity 102 of FIG. 1), and a second set of operations (e.g., operations 320-328) may be performed by another entity (e.g., a part manufacturing entity, such as the part manufacturing entity 104 of FIG. 1). In other cases, while not shown in the example of FIG. 3, it will be appreciated that a single entity may manufacture the pellets and also utilize the pellets to manufacture an article from the pellets. Thus, FIG. 3 illustrates one example of the utilization of a water-sensitive fluorophore for non-destructive moisture content testing of a material (e.g., a pellet) that includes a hygroscopic polymer material (e.g., a nylon material).

The process 300 includes forming a blend that includes a hygroscopic polymer resin and a water-sensitive fluorophore, at 302. For example, referring to FIG. 1, the hygroscopic polymer resin 110 and the water-sensitive fluorophore 112 form the blend 114. The hygroscopic polymer resin 110 may include a nylon resin, an ABS polymer resin, an acrylics resin, a polyurethane resin, a PET resin, or a PBT resin, among other examples. With respect to the water-sensitive fluorophore 112, illustrative examples may include 5-(dimethylamino)naphthalene-1-sulfonic acid (DNSA), 5-(dimethylamino)naphthalene-1-sulfonamide (DNSM), 8-(anilino)naphthalene-1-sulfonic acid (ANSA), or a combination thereof, among other alternatives.

The process 300 includes forming pellets having a particular geometry from the blend, at 304. For example, referring to FIG. 1, the extruder 118 may be used to form the pellets 120 having the particular pellet geometry 122 from the blend 114.

The process 300 further includes determining fluorescence properties of the pellets, at 306. For example, referring to FIG. 1, the analysis component(s) 130 of the pellet manufacturing entity 102 may be utilized to determine the fluorescence properties 132 of the pellets 120. For example, the fluorescence properties 132 of the pellets 120 may include fluorescence intensity data and/or emission maximum data for a particular concentration of the water-sensitive fluorophore 112 in the blend 114, among other examples.

The process 300 further includes measuring moisture content of a pellet, at 308. For example, referring to FIG. 1, the moisture content 140 of at least one of the pellets 120 may be determined by Karl Fischer titration using the Karl Fischer titration component(s) 142. In the example of FIG. 1, such moisture content testing is performed on one of the pellets 120. In other cases, it will be appreciated that more than one of the pellets 120 may be used in the Karl Fischer titration process.

While FIG. 3 illustrates operations 306 and 308 being performed in parallel, it will be appreciated that the operations 306 and 308 may be performed in alternative orders, at alternative times, by one or more other entities (not shown in FIG. 1), or a combination thereof. To illustrate, in some cases, the pellet manufacturing entity 102 may select one or more of the pellets 120 to be sent for moisture content determination using the Karl Fischer titration component(s) 142, then determine the fluorescence properties 132 of one or more of the remaining pellets 120. As another example, the pellet manufacturing entity 102 may not have access to the Karl Fischer titration component(s) 142 and may therefore send one or more of the selected pellets 120 to another entity (e.g., a testing laboratory) for determination of the moisture content 140 for subsequent association with the fluorescence properties 132.

FIG. 3 illustrates that, after determining the fluorescence properties of the pellets (at 306) and measuring the moisture content of one or more selected pellets (at 308), the process 300 further includes generating a calibration curve for the particular pellet geometry, at 310. The calibration curve for the particular pellet geometry may be determined by correlating the fluorescence properties with the moisture content. For example, referring to FIG. 1, the fluorescence properties 132 determined by the analysis component(s) 130 and the moisture content 140 determined by the Karl Fischer titration component(s) 142 may be provided to the computing device 150. The computing device 150 may generate the calibration curve 152 for the particular pellet geometry 122 by correlating the fluorescence properties 132 with the moisture content 140.

Referring to the second set of operations depicted below the dashed line in FIG. 3, the part manufacturing entity may receive the pellets from the pellet manufacturing entity after the calibration curve has been generated (at 310). For example, referring to FIG. 1, the part manufacturing entity 104 may receive the pellets 120 from the pellet manufacturing entity 102 after the pellet manufacturing entity 102 has generated the calibration curve 152 for the pellets 120.

The process 300 includes drying the pellets, at 320. For example, referring to FIG. 1, the part manufacturing entity 104 may utilize the moisture removal component(s) 160 to form the dried pellets 162 from the pellets 120.

The process 300 includes measuring the fluorescence properties of the dried pellets, at 322. For example, referring to FIG. 1, the part manufacturing entity 104 may utilize the analysis component(s) 170 to determine fluorescence properties 172 of the dried pellets 162.

The process 300 includes utilizing the calibration curve (generated in operation 310) to determine moisture level of the dried pellets based on the measured fluorescence properties, at 324. For example, referring to FIG. 1, the calibration curve 152 generated by the pellet manufacturing entity 102 may be utilized to determine the moisture content 176 of the dried pellets 162 based on the fluorescence properties 172 measured by the analysis component(s) 170 of the part manufacturing entity 104. In the particular embodiment depicted in FIG. 3, where one set of operations is performed by one entity and another set of operations is performed by another entity, a dashed line is used to represent that the calibration curve is available to both entities. In some cases, the pellet manufacturing entity (e.g., the pellet manufacturing entity 102 of FIG. 1) may provide the calibration curve to the part manufacturing entity (e.g., the part manufacturing entity 104 of FIG. 1) along with the pellets. In other cases, the calibration curve may be otherwise accessible to the part manufacturing entity, such as via network access to the pellet database 154 depicted in FIG. 1.

The process 300 further includes determining whether the moisture level of the dried pellets is satisfactory, at 326. For example, referring to FIG. 1, prior to forming the article of manufacture 106 (e.g., via injection molding), the part manufacturing entity 104 may determine whether the moisture content 176 of the dried pellets 162 is satisfactory. In the event that the moisture content is unsatisfactory, FIG. 3 illustrates that the process 300 may include performing an additional pellet drying operation, at 320. For example, referring to FIG. 1, when the moisture content 176 is determined to be unsatisfactory for injection molding, the part manufacturing entity 104 may perform additional pellet drying operation(s) using the moisture removal component(s) 160. After performing the additional pellet drying operation(s), the process 300 may include performing an additional measurement of the fluorescence properties, at 322, and utilizing the calibration curve to determine moisture level based on the additional measurement of the fluorescence properties, at 324. The process 300 may iterate until the dried pellets are determined to have a satisfactory moisture level for forming the article of manufacture 106 (e.g., via injection molding).

When the moisture level is determined to be satisfactory, at 326, FIG. 3 illustrates that the process 300 may include manufacturing an article from the dried pellets, at 328. For example, referring to FIG. 1, the part manufacturing entity 104 may utilize the molding component(s) 164 to form the article of manufacture 106. As an illustrative, non-limiting example, the article of manufacture 106 may include a nylon pull tab (e.g., a nylon 6,6 pull tab) for cable management behind a server rack (as depicted in the example deployment environment 202 of FIG. 2).

Thus, FIG. 3 illustrates an example of a process of utilizing a water-sensitive fluorophore with a hygroscopic polymer for determining whether a moisture content level is satisfactory. FIG. 3 illustrates a first example of non-destructive moisture content determination in which a part manufacturing entity uses the calibration curve generated by the pellet manufacturing entity to determine whether the pellets have been sufficiently dried prior to injection molding. As further described herein, FIG. 4 illustrates a second example of non-destructive moisture content determination in which a part monitoring entity uses a part-specific calibration curve generated by the part manufacturing entity to determine whether a moisture level of an article that is deployed in a particular environment is satisfactory or that a corrective action may be required (e.g., removal/replacement of the article from the field).

Figure 4:
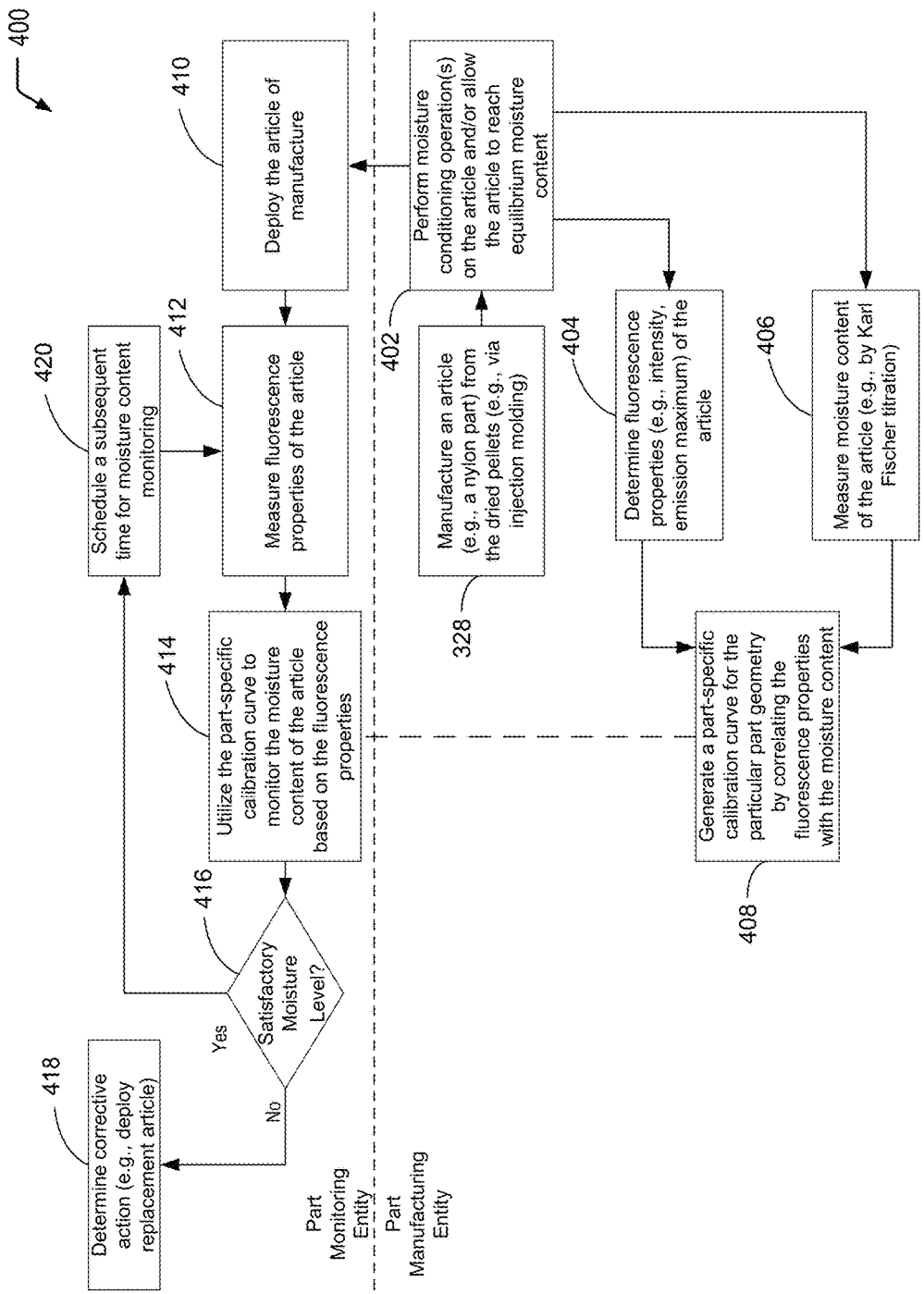
FIG. 4 is a flow diagram depicting a particular embodiment of a process of utilizing water-sensitive fluorophores with hygroscopic polymers for determining whether moisture content level is satisfactory.

Referring to FIG. 4, a flow diagram illustrates an example of a process 400 of utilizing water-sensitive fluorophores with hygroscopic polymers for determining whether moisture content level is satisfactory, according to one embodiment. FIG. 4 illustrates (via a dashed line) that, in some cases, a first set of operations (e.g., operations 328 and 402-408) may be performed by one entity (e.g., a part manufacturing entity, such as the part manufacturing entity 104 of FIG. 1), and a second set of operations (e.g., operations 410-420) may be performed by another entity (e.g., a part monitoring entity, as described further herein with respect to FIG. 2. In other cases, while not shown in the example of FIG. 4, it will be appreciated that a single entity may manufacture the parts and also monitor the parts after field-deployment. Thus, FIG. 4 illustrates another example of the utilization of a water-sensitive fluorophore for non-destructive moisture content testing of a material (e.g., a deployed part) that includes a hygroscopic polymer material (e.g., a nylon material).

In the particular embodiment depicted in FIG. 4, selected operations performed by a part manufacturing entity have been omitted. For example, with respect to the second set of operations depicted in FIG. 3, FIG. 4 illustrates only operation 328 from FIG. 3, representing the last operation performed by the part manufacturing entity (e.g., the part manufacturing entity 104 of FIG. 1).

Referring to the portion of FIG. 4 below the dashed line delineating the part monitoring entity from the part manufacturing entity, the process includes performing moisture conditioning operation(s) on the article and/or allowing the article to reach an equilibrium moisture content, at 402. For example, referring to FIG. 1, after forming the article of manufacture 106 (e.g., via injection molding, the part manufacturing entity 104 may perform moisture conditioning operation(s) on the article 106 and/or allow the article 106 to reach an equilibrium moisture content. As described further herein, while drying the pellets 120 is important for injection molding, the presence of at least some moisture in the article of manufacture 106 may be desirable (e.g., for toughness and/or flexibility) before the article 106 is deployed in order to reduce the likelihood of brittle fracture in some deployment environments (e.g., the deployment environment 202 depicted in FIG. 2).

The process 400 includes determining fluorescence properties of the article, at 404. For example, referring to FIG. 1, the analysis component(s) 170 of the part manufacturing entity 104 may be utilized to determine the fluorescence properties 182 of the article of manufacture 106. For example, the fluorescence properties 182 of the article 106 may include fluorescence intensity data and/or emission maximum data, among other examples.

The process 400 further includes measuring moisture content of the article, at 406. For example, referring to FIG. 1, the part manufacturing entity 104 may determine the moisture content 184 of the article of manufacture 106 by Karl Fischer titration using the Karl Fischer titration component(s) 186. Such destructive moisture content testing may be performed on at least one article of manufacture 106 formed using the molding component(s) 164.

While FIG. 4 illustrates operations 404 and 406 being performed in parallel, it will be appreciated that the operations 404 and 406 may be performed in alternative orders, at alternative times, by one or more other entities (not shown in FIG. 1), or a combination thereof. To illustrate, in some cases, the part manufacturing entity 104 may first determine the fluorescence properties 182 of the article of manufacture 106, then perform destructive moisture content testing on a sacrificial article 106 using the Karl Fischer titration component(s) 186. In other cases, the fluorescence properties may be determined for one or more articles, and another sacrificial article (or multiple articles) may be sent for destructive moisture content testing using the Karl Fischer titration component(s) 186. As another example, while not shown in the embodiment depicted in FIG. 1, the part manufacturing entity 104 may not have access to equipment for performing a Karl Fischer titration process on the article of manufacture 106 and may therefore send the article 106 to another entity (e.g., a testing laboratory) for determination of the moisture content 184 for subsequent association with the fluorescence properties 182.

FIG. 4 illustrates that, after determining the fluorescence properties of the article (at 404) and measuring the moisture content of the article (at 406), the process 400 further includes generating a part-specific calibration curve for the particular part geometry, at 408. The part-specific calibration curve for the particular part geometry may be determined by correlating the fluorescence properties with the moisture content. For example, referring to FIG. 1, the fluorescence properties 182 determined by the analysis component(s) 170 and the moisture content 184 determined by the Karl Fischer titration component(s) 186 may be provided to the computing device 174 of the part manufacturing entity 104. The computing device 174 may generate the part-specific calibration curve 190 for the particular part geometry 180 by correlating the fluorescence properties 182 with the moisture content 184.

Referring to the second set of operations depicted above the dashed line in FIG. 4, the part monitoring entity may receive the article of manufacture from the part manufacturing entity after the part-specific calibration curve has been generated (at 408). For example, referring to FIG. 1, the part manufacturing entity 104 may provide the article of manufacture 106 to another entity for field deployment after generating the part-specific calibration curve 190.

The process 400 includes deploying the article of manufacture, at 410. For example, referring to FIG. 2, the article of manufacture 106 of FIG. 1 may be deployed in the deployment environment 202 where the article 106 is exposed to a particular set of environmental conditions. As an illustrative, non-limiting example, the article of manufacture 106 may include a nylon pull tab (e.g., a nylon 6,6 pull tab) for cable management, and the deployment environment 202 may correspond to an area behind a server rack. In this example, the article of manufacture 106 may experience high temperature and/or low humidity as a result of the server exhaust. In some cases, such environmental conditions may cause the article of manufacture 106 to embrittle as a result of moisture removal, potentially resulting in fracture/failure of the article of manufacture 106.

The process 400 includes measuring the fluorescence properties of the article, at 412. For example, referring to FIG. 2, the stimulation component 212 may be utilized to excite the water-sensitive fluorophore 112 in the water-sensitive fluorophore fluorescence area 216. The fluorescence measurement component 214 may collect the fluorescence properties 220 for the article of manufacture 106. As described further herein with respect to FIG. 2, the stimulation component 212 and the fluorescence measurement component 214 may be included within or otherwise communicatively coupled to the computing device 210. The computing device 210 may be utilized by the field technician 204 for non-destructive moisture content determination in the article of manufacture 106 in the deployment environment 202.

The process 400 includes utilizing the part-specific calibration curve to monitor the moisture content of the article based on the fluorescence properties, at 414. For example, in the particular embodiment depicted in FIG. 2, the measured fluorescence properties 220 for the field-deployed article of manufacture 106 may be used to query the part database 192 of FIG. 1. As described herein with respect to FIG. 1, the part database 192 stores the part-specific calibration curve 190, which may be utilized to determine the moisture content 222 based on the fluorescence properties 220 for the article of manufacture 106 in the deployment environment 202.

In the particular embodiment depicted in FIG. 4, where different operations are performed by different entities, a dashed line is used to represent that the part-specific calibration curve is available to the part monitoring entity. In some cases, the part manufacturing entity may provide the part-specific calibration curve to the part monitoring entity along with the article of manufacture. In other cases, the part-specific calibration curve may be otherwise accessible to the part monitoring entity, such as via network access to the part database 192, as shown in the example embodiment of FIG. 2.

The process 400 further includes determining whether the moisture level of the deployed article is satisfactory, at 416. In the event that the moisture level is unsatisfactory, FIG. 4 illustrates that the process 400 may include determining corrective action, at 418. For example, referring to FIG. 2, the field technician 204 may determine whether to remove the article of manufacture 106 from the deployment environment 202, to replace the deployed article of manufacture 106 with an article that is known to have a satisfactory moisture level, or perform additional and/or alternative corrective actions.

In the event that the moisture level is determined to be satisfactory, at 416, FIG. 4 illustrates a particular embodiment in which the process 400 further includes scheduling a subsequent time for moisture content monitoring, at 420. In other cases, the process 400 may end, at 416. For example, after deployment of the article into an environment having a particular set of environmental conditions that may be relatively stable (e.g., in a data center environment), it may be appropriate to infer that there is a low risk of part failure when the moisture content level of the article is shown to be satisfactory in the environment after being exposed to the particular set of environmental conditions for a sufficient period of time.

Thus, FIG. 4 illustrates an example of a process of utilizing water-sensitive fluorophores with hygroscopic polymers for determining whether moisture content level is satisfactory.

FIG. 4 illustrates another example of non-destructive moisture content determination in which a part monitoring entity uses a part-specific calibration curve generated by a part manufacturing entity to determine whether a moisture level of an article that is deployed in a particular environment is satisfactory or that a corrective action may be required (e.g., removal/replacement of the article from the field).

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of utilizing a water-sensitive fluorophore for moisture content evaluation in a hygroscopic polymer, the process comprising:
    forming a blend that includes a hygroscopic polymer resin and a water-sensitive fluorophore;
    forming pellets having a particular geometry from the blend;
    determining fluorescence properties of at least one of the pellets;
    determining moisture content of at least one of the pellets;
    generating a calibration curve for the particular pellet geometry by correlating the fluorescence properties with the moisture content; and
    providing the calibration curve for non-destructive moisture content evaluation of a material derived from the pellets.

2. The process of claim 1, wherein the calibration curve is provided to a part manufacturing entity for moisture content evaluation after forming dried pellets by removing moisture from the pellets prior to forming an article of manufacture from the dried pellets.

3. The process of claim 2, wherein the article of manufacture is formed by injection molding.

4. The process of claim 2, wherein the part manufacturing entity measures fluorescence properties of the dried pellets and utilizes the calibration curve to determine a moisture content level of the dried pellets based on the measured fluorescence properties of the dried pellets.

5. The process of claim 4, further comprising forming the article of manufacture from the dried pellets when the moisture content level of the dried pellets is a satisfactory moisture level.

6. The process of claim 4, further comprising performing an additional drying operation to remove additional moisture from the dried pellets when the moisture content level of the dried pellets is an unsatisfactory moisture level.

7. The process of claim 1, wherein the hygroscopic polymer resin includes a nylon resin.

8. The process of claim 1, wherein the hygroscopic polymer resin includes an acrylonitrile butadiene styrene (ABS) resin, an acrylic resin, a polyurethane resin, a polyethylene terephthalate (PET) resin, or a polybutylene terephthalate (PBT) resin.

9. The process of claim 1, wherein the water-sensitive fluorophore includes 5-(dimethylamino)naphthalene-1-sulfonic acid (DNSA), 5-(dimethylamino)naphthalene-1-sulfonamide (DNSM), 8-(anilino)naphthalene-1-sulfonic acid (ANSA), or a combination thereof.

10. The process of claim 1, wherein the moisture content of at least one of the pellets is determined by Karl Fischer titration.

11. A process of utilizing a water-sensitive fluorophore for moisture content evaluation in a hygroscopic polymer, the process comprising:
    receiving, from a pellet manufacturing entity, pellets that are formed from a blend that includes a hygroscopic polymer resin and a water-sensitive fluorophore;
    receiving, from the pellet manufacturing entity, a calibration curve that correlates fluorescence properties of the pellets with moisture content of the pellets;
    forming dried pellets by removing moisture from the pellets prior to forming an article of manufacture from the dried pellets;
    measuring fluorescence properties of the dried pellets;
    utilizing the calibration curve to determine a moisture content level of the dried pellets based on the measured fluorescence properties of the dried pellets; and
    determining whether to form the article of manufacture from the dried pellets based on whether the moisture content level of the dried pellets corresponds to a satisfactory moisture level.

12. The process of claim 11, further comprising performing an additional drying operation to remove additional moisture from the dried pellets when the moisture content level of the dried pellets corresponds to an unsatisfactory moisture level.

13. The process of claim 11, further comprising forming the article of manufacture from the dried pellets when the moisture content level of the dried pellets corresponds to the satisfactory moisture level, the article of manufacture having a particular part geometry.

14. The process of claim 13, further comprising performing one or more moisture conditioning operations on the article of manufacture, allowing the article of manufacture to reach an equilibrium moisture content, or a combination thereof.

15. The process of claim 14, further comprising:
    determining fluorescence properties of the article of manufacture;
    determining moisture content of the article of manufacture; and
    generating a part-specific calibration curve for the particular part geometry by correlating the fluorescence properties of the article of manufacture with the moisture content of the article of manufacture.

16. The process of claim 15, further comprising providing the part-specific calibration curve to a part monitoring entity for non-destructive moisture content evaluation of the article of the manufacture in a deployment environment.

17. The process of claim 16, wherein the part monitoring entity measures fluorescence properties of the article of manufacture in the deployment environment and utilizes the part-specific calibration curve to determine a moisture content level of the article of manufacture based on the measured fluorescence properties of the article of manufacture in the deployment environment.

18. A process of utilizing a water-sensitive fluorophore for moisture content evaluation in a hygroscopic polymer, the process comprising:
    measuring fluorescence properties of an article of manufacture that is deployed to a deployment environment, wherein the article of manufacture is manufactured from pellets that are formed from a blend that includes a hygroscopic polymer resin and a water-sensitive fluorophore;

receiving a part-specific calibration curve that correlates fluorescence properties of the article of manufacture with moisture content of the article of manufacture;

utilizing the part-specific calibration curve to determine a moisture content level of the article of manufacture based on the measured fluorescence properties of the article of manufacture; and determining whether to perform a corrective action based on whether the moisture content level of the article of manufacture corresponds to a satisfactory moisture level.

19. The process of claim 18, wherein the corrective action includes removal of the article of manufacture from the deployment environment.

20. The process of claim 18, wherein the environmental conditions associated with the deployment environment correspond to a high temperature environment, a low humidity environment, or a combination thereof, and wherein the environmental conditions are associated with a high probability of the article of manufacture becoming brittle as a result of moisture removal.

* * * * *